(12) United States Patent
Vodinh

(10) Patent No.: US 9,027,254 B1
(45) Date of Patent: May 12, 2015

(54) SCALPEL HANDLE HAVING A BLADE SHIELD

(71) Applicant: Hien Vodinh, Knoxville, TN (US)

(72) Inventor: Hien Vodinh, Knoxville, TN (US)

(73) Assignee: Bosela Design LLC, Chattanooga, TN (US)

( * ) Notice: Subject to any disclaimer, the term of this patent is extended or adjusted under 35 U.S.C. 154(b) by 0 days.

(21) Appl. No.: 13/998,559

(22) Filed: Nov. 8, 2013

(51) Int. Cl.
*B26B 29/02* (2006.01)
*A61B 17/32* (2006.01)
*A61B 17/3211* (2006.01)

(52) U.S. Cl.
CPC ............. *A61B 17/3211* (2013.01); *B26B 29/02* (2013.01)

(58) Field of Classification Search
CPC ............................ B26B 29/02; A61B 17/3211
USPC ............... 30/2, 151, 284–286, 143, 330, 283; 606/167
See application file for complete search history.

(56) References Cited

U.S. PATENT DOCUMENTS

| | | | |
|---|---|---|---|
| 1,452,893 A | 4/1923 | Porth | |
| 4,980,977 A | 1/1991 | Matin et al. | |
| 5,139,507 A * | 8/1992 | Dolgin et al. | 606/167 |
| 5,250,064 A | 10/1993 | Schneider | |
| 6,718,637 B1 | 4/2004 | Ortner et al. | |
| 7,024,772 B1 * | 4/2006 | Shaver et al. | 30/2 |
| 7,485,126 B2 * | 2/2009 | Adelman et al. | 606/172 |
| 7,509,742 B2 * | 3/2009 | Votolato | 30/151 |
| 7,810,241 B2 * | 10/2010 | Pooler | 30/151 |
| 8,347,509 B2 * | 1/2013 | Votolato | 30/156 |
| 2012/0279071 A1 * | 11/2012 | Garavaglia et al. | 30/162 |
| 2012/0317820 A1 * | 12/2012 | McGushion et al. | 30/164 |
| 2013/0185943 A1 * | 7/2013 | Landwehr | 30/153 |

* cited by examiner

*Primary Examiner* — Laura M Lee
(74) *Attorney, Agent, or Firm* — Michael E. McKee

(57) ABSTRACT

A scalpel handle for holding a blade having a cutting edge includes a handle member and a blade shield for covering the blade cutting edge. The blade shield is connected to the handle member for pivotal movement relative thereto between a blade-covering condition and an out-of-the-way condition, and a movable shield latch mechanism is capable of releasably locking the blade shield in its blade-covering condition. A finger-operable actuator mechanism is mounted upon the handle member for movement between first and second conditions, and a spring is interposed between the actuator mechanism and the handle member. During a first phase of movement of the actuator mechanism from its first to its second condition, the shield latch mechanism unlocks the blade shield from its locked blade-covering condition, and during a second phase of movement, the blade shield is moved from its blade-covering condition to its out-of-the-way condition.

18 Claims, 8 Drawing Sheets

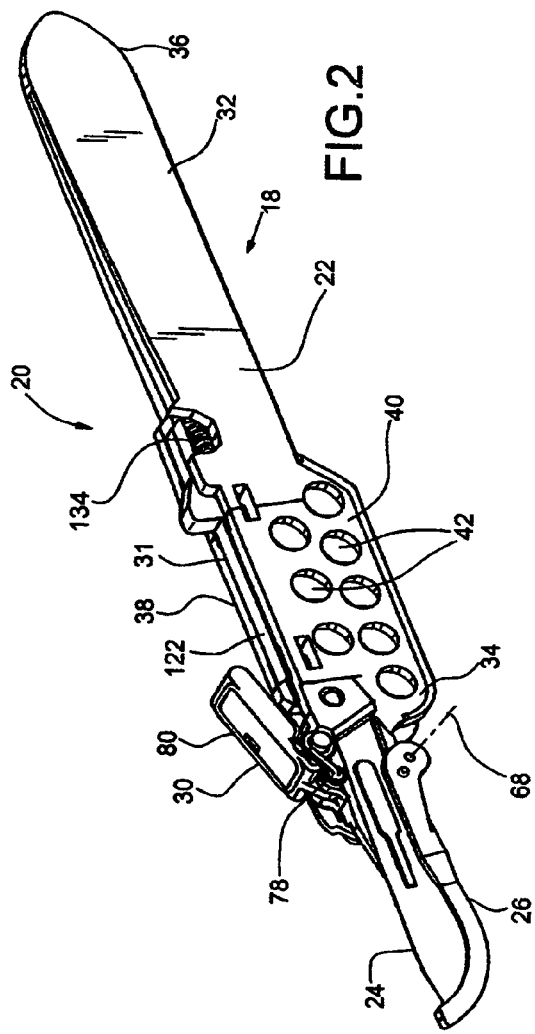

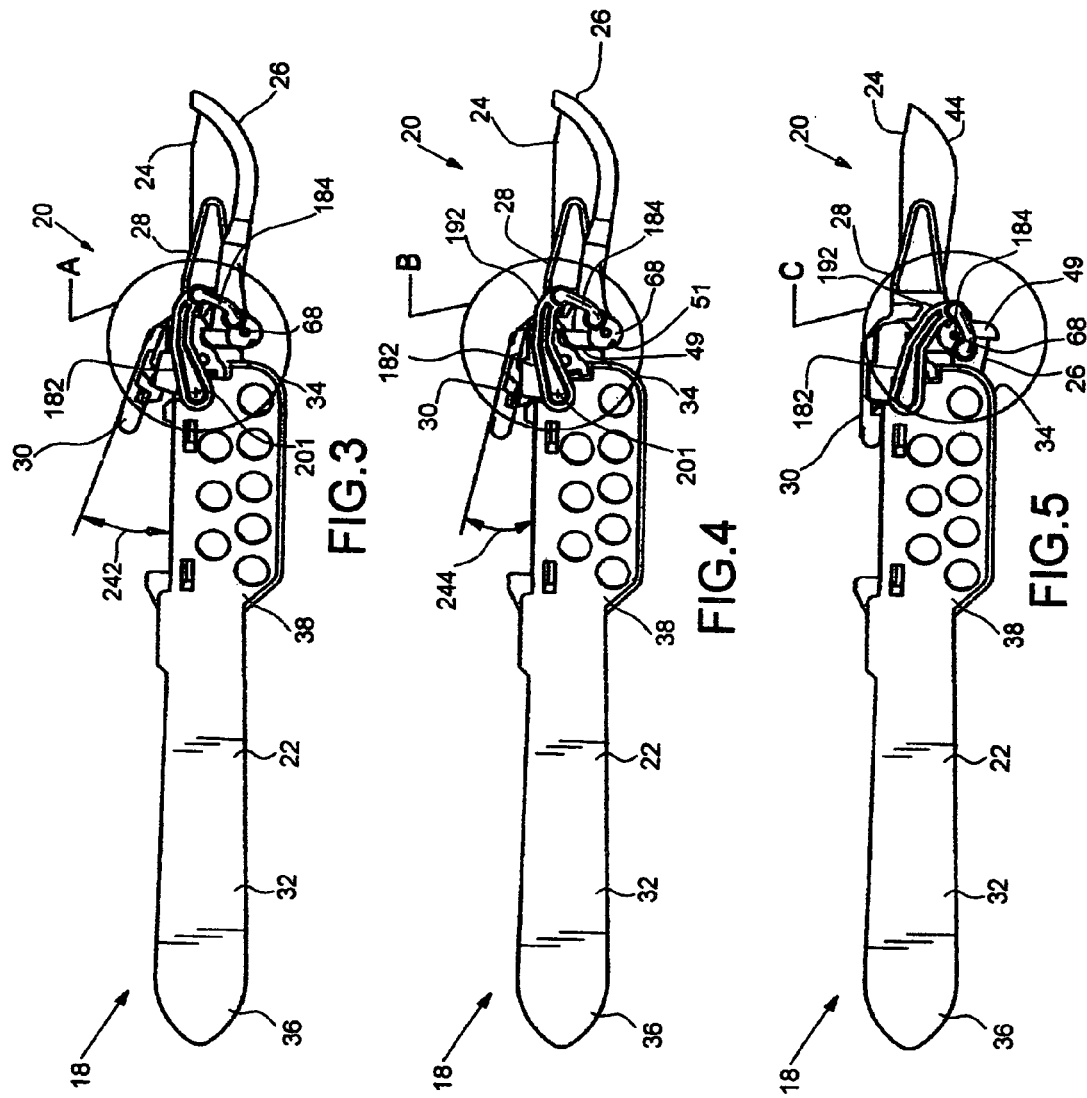

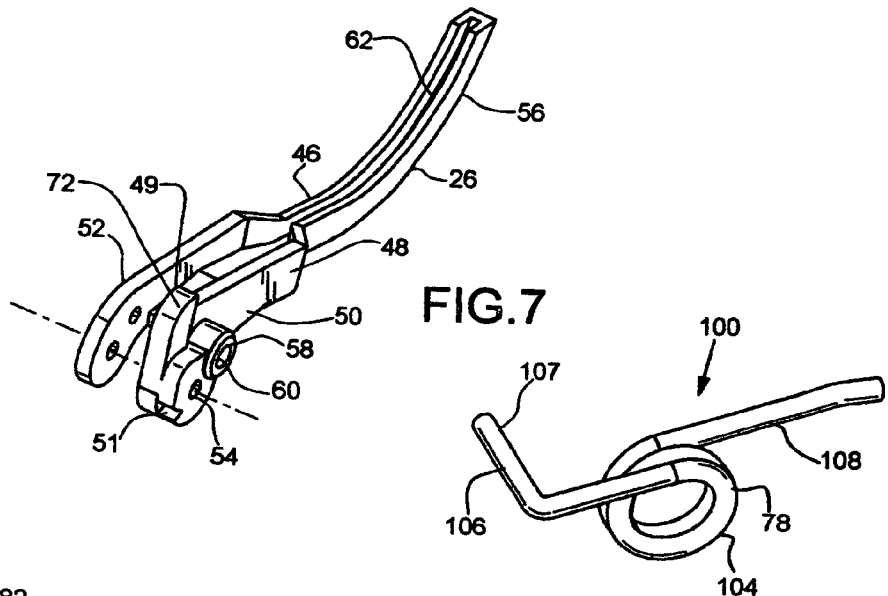
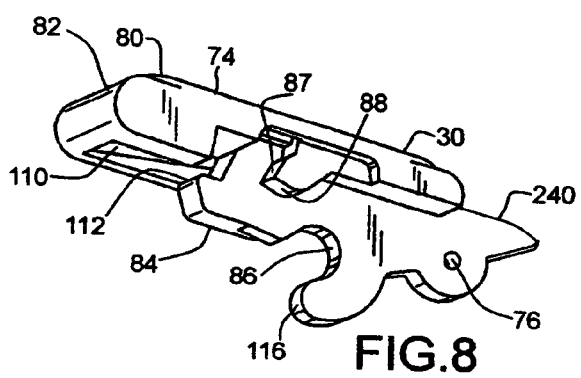
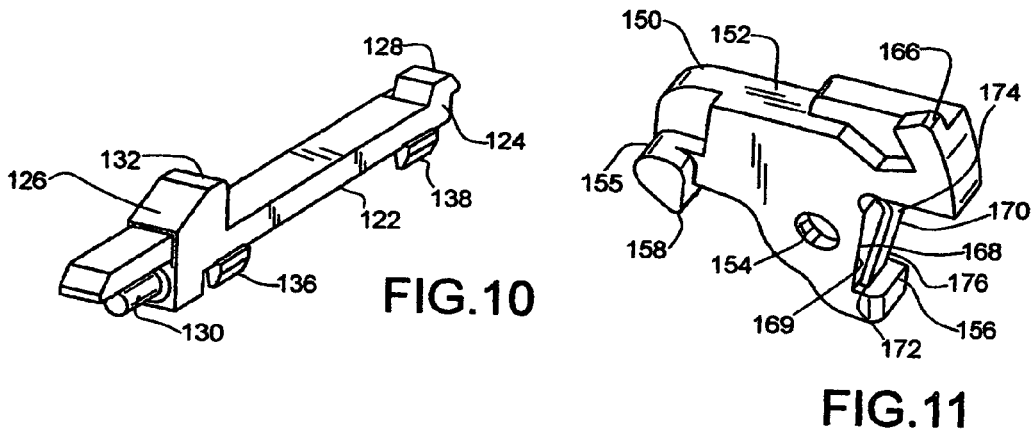

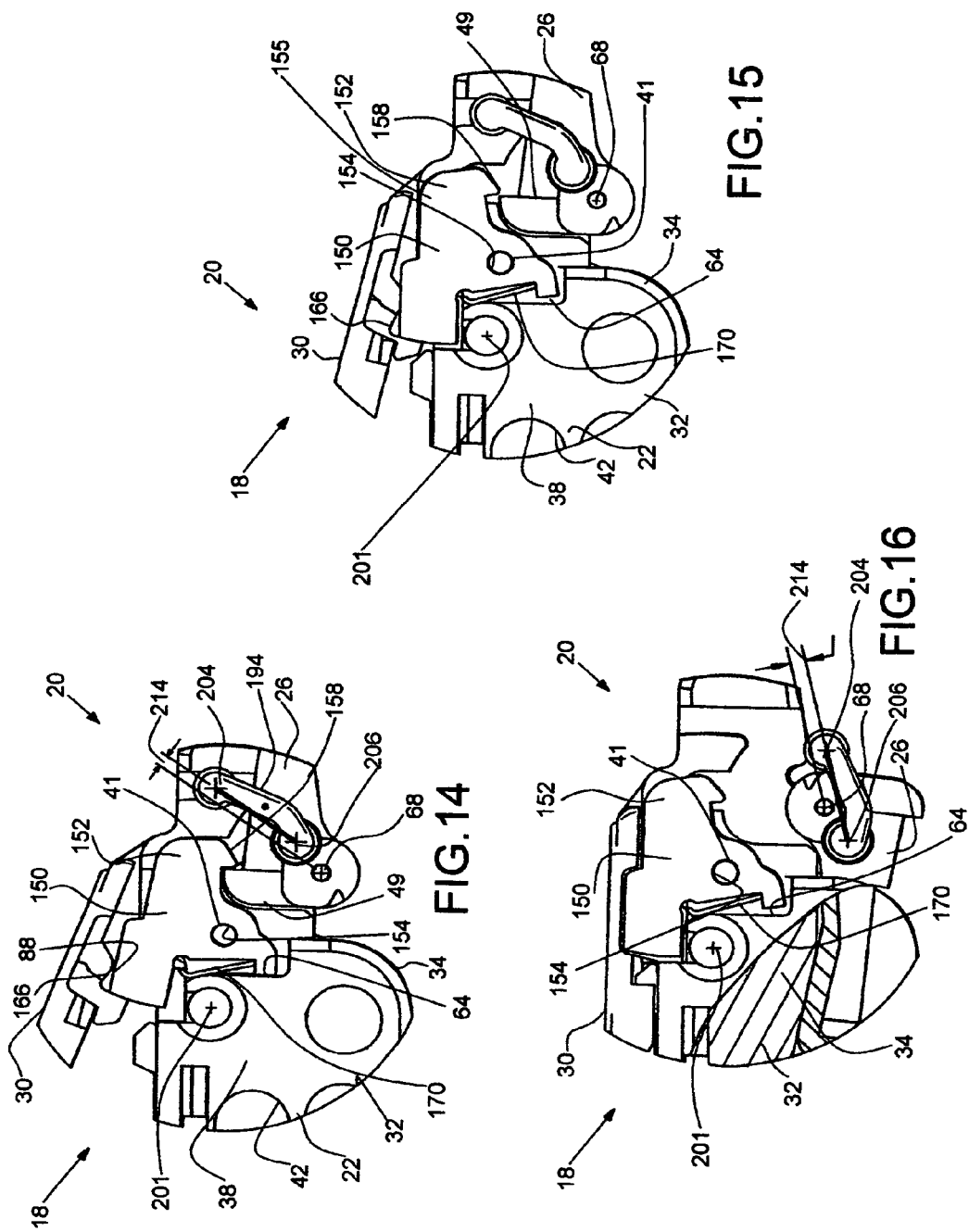

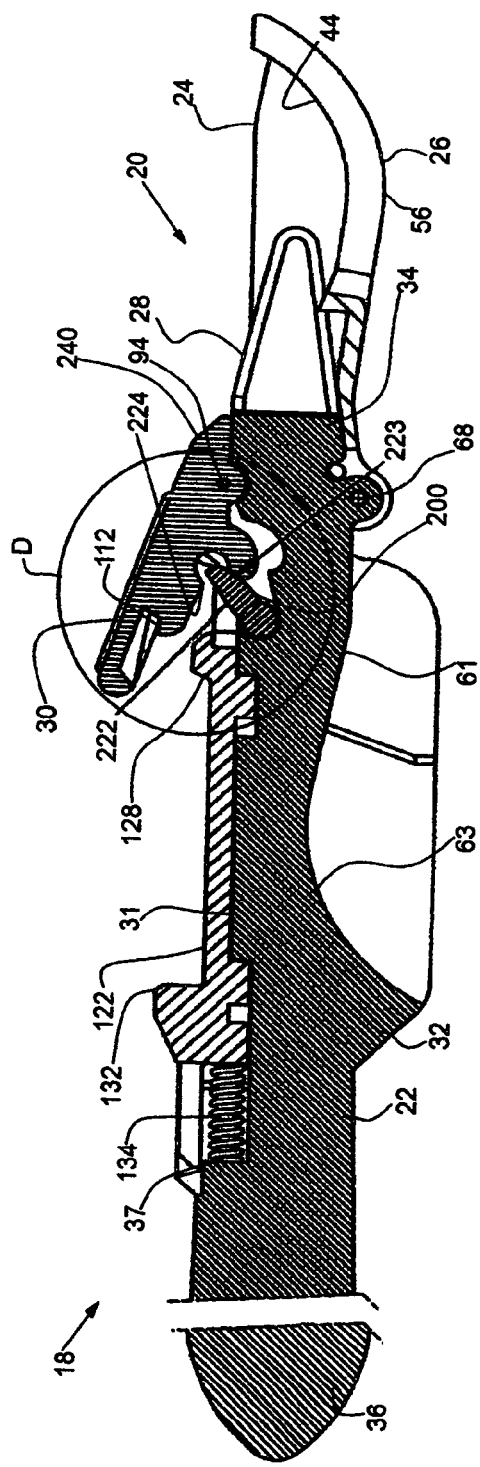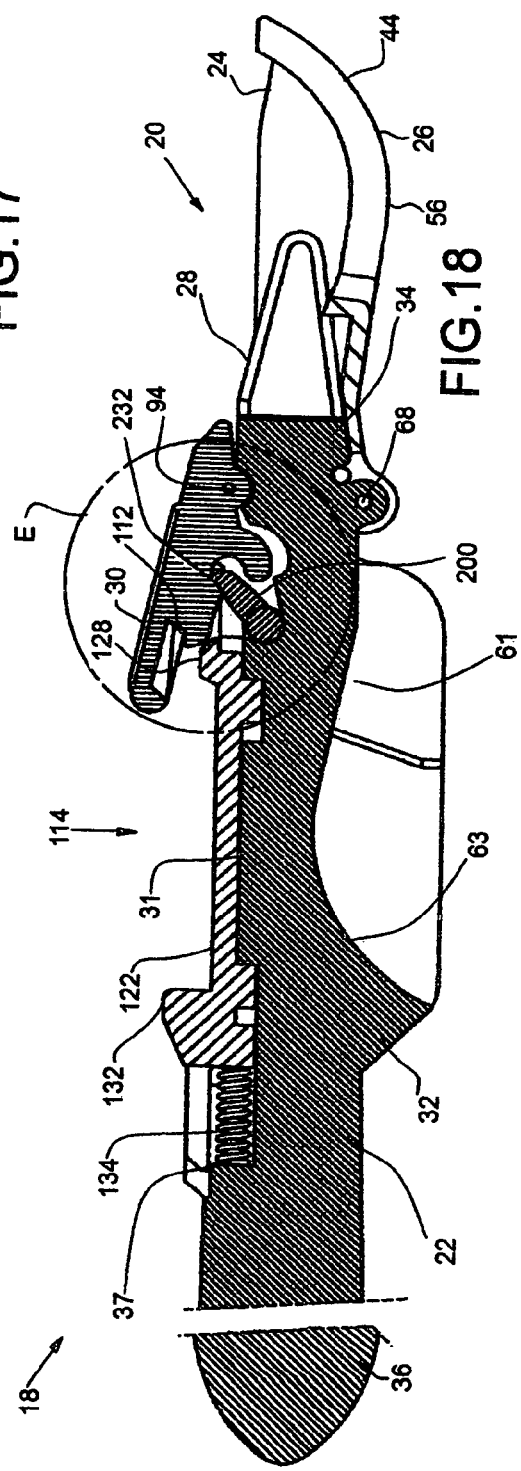

SCALPEL HANDLE HAVING A BLADE SHIELD

BACKGROUND OF THE INVENTION

This invention relates generally to surgical scalpels and relates, more particularly, to means and methods by which the cutting edge of a scalpel blade is covered between periods of use.

It is known that in order to reduce the risk of inadvertent cuts from a scalpel in a surgical environment as, for example, the scalpel is passed from one individual to another, the cutting blade of the scalpel can be covered with a safety shield between periods of use, and it is this class of shielded scalpels to which the present invention is to be compared. One such shielded scalpel is described in U.S. Pat. No. 7,810,241 as having an elongated handle, a cutting blade which extends from the handle and a safety shield which is attached to the handle for movement relative thereto between a blade edge-covering position and an out-of-the way position at which the cutting edge of the blade is exposed for use. Furthermore, a manually-operable slide assembly is mounted upon the handle for sliding movement along the length thereof, and gear mechanisms are interposed between the slide mechanism and the safety shield so that the movement of the shield between its edge-covering and out-of-the-way positions is effected by the movement of the slide assembly along the length of the handle.

It is an object of the present invention to provide a new and improved scalpel handle having a safety shield for covering the blade mounted upon the handle.

Another object of the present invention is to provide such a scalpel handle having a safety shield which is movable between a blade-covering position and an out-of-the-way position at which the cutting edge of the blade is exposed for use and which employs an improved scheme for moving the shield between its blade-covering and its out-of-the-way position.

Still another object of the present invention is to provide such a scalpel handle whose shield can be readily moved by an operator between its blade-covering and its out-of-the-way position.

Yet another object of the present invention is to provide such a scalpel handle having an actuator mechanism which can be depressed by a finger (e.g. the index finger) of the hand which grasps the handle for moving the blade shield from its blade-covering position to its out-of-the-way position and whose blade shield can be releasably locked in its out-of-the-way position.

A further object of the present invention is to provide such a scalpel handle whose blade shield can be readily unlocked from its locked, out-of-the-way position.

A still further object of the present invention is to provide such a scalpel handle having a grip which is designed to reduce the likelihood of slip between the handle and the grasping hand and to facilitate the manipulation of the scalpel handle with the grasping hand during use.

A yet further object of the present invention is to provide such a scalpel handle which is uncomplicated in structure, yet effective in operation.

SUMMARY OF THE INVENTION

This invention resides in a scalpel handle for holding a blade having a cutting edge.

The scalpel handle includes a handle member to which a blade is securable for use and a blade shield for covering the cutting edge of the blade when the blade is secured to the handle member. In addition, the blade shield is connected to the handle member for pivotal movement relative thereto between a blade-covering condition at which the blade shield covers the cutting edge of the blade and an out-of-the way condition at which the cutting edge of the blade is exposed for use. The handle further includes a manually-operable actuator mechanism which is mounted upon the handle member for movement relative thereto between a first condition and a second condition, and a linkage assembly is interposed between the actuator mechanism and the blade shield. The actuator mechanism is adapted to cooperate with the linkage assembly so that by manually moving the actuator mechanism from the first condition toward the second condition, the blade shield is moved by way of the linkage assembly from its blade-covering condition toward its out-of-the-way condition.

BRIEF DESCRIPTION OF THE DRAWINGS

FIG. 2 is an alternative perspective view of the scalpel assembly of FIG. 1, but having a portion cut-away.

FIGS. 3-5 are side elevation views of the FIG. 1 scalpel assembly as seen generally from the left in FIG. 1 illustrating the blade shield of the assembly when positioned in either its blade-covering condition (FIGS. 3 and 4) or its out-of-the-way condition (FIG. 5) and illustrating sequential positions of the finger-depressible actuator mechanism when depressed for the purpose of moving the blade shield from the blade-covering condition to its out-of-the-way condition.

FIG. 7 is a perspective view of the blade shield of the FIG. 1 scalpel assembly.

FIG. 8 is a perspective view of the finger-depressible actuator mechanism of the FIG. 1 scalpel assembly.

FIG. 9 is a perspective view of the torsion spring of the FIG. 1 scalpel assembly.

FIG. 10 is a perspective view of the actuator latch mechanism of the FIG. 1 scalpel assembly.

FIG. 11 is a perspective view of the shield latch mechanism of the FIG. 1 scalpel assembly.

FIG. 14 is an enlarged view of the componentry of the FIG. 1 scalpel assembly shown in the circle A of FIG. 3, but with the lever arm removed therefrom.

FIG. 15 is an enlarged view of the componentry of the FIG. 1 scalpel assembly shown in the circle B of FIG. 4, but with the lever arm removed therefrom.

FIG. 16 is an enlarged view of the componentry of the FIG. 1 scalpel assembly shown in the circle C of FIG. 5, but with the lever arm removed therefrom and a fragment of the handle member and blade shield shown in longitudinal cross section.

FIG. 17 is a longitudinal cross-sectional view of the FIG. 1 scalpel assembly corresponding to the position of the scalpel assembly componentry depicted in FIG. 3.

FIG. 18 is a longitudinal cross-sectional view of the FIG. 1 scalpel assembly corresponding to the position of the scalpel assembly componentry depicted in FIG. 4.

FIG. 19 is a longitudinal cross-sectional view of the FIG. 1 scalpel assembly corresponding to the position of the scalpel assembly componentry depicted in FIG. 5.

DETAILED DESCRIPTION OF AN ILLUSTRATIVE EMBODIMENT

Figure 1:
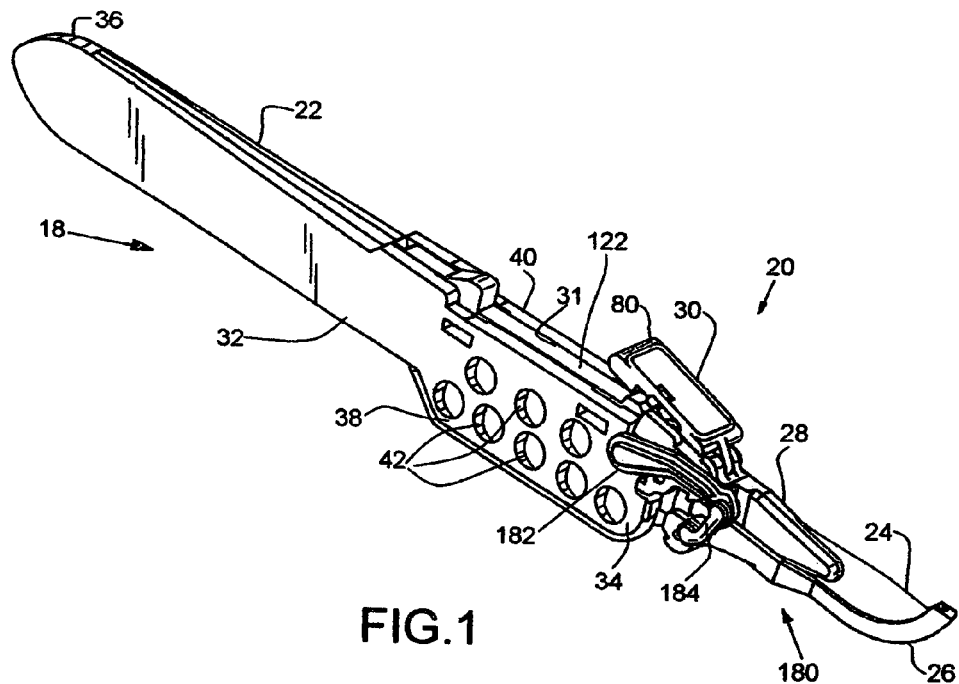
FIG. 1 is a perspective view of a scalpel assembly within which features of the present invention are embodied.

Turning now to the drawings in greater detail and considering first FIGS. 1-5, there is illustrated an embodiment, generally indicated 20, of a scalpel, or scalpel assembly, within which features of the present invention are embodied. Briefly, the scalpel 20 includes means, generally indicated 18, providing a handle of the scalpel 20 and an elongated blade 24 which is connected to the handle-providing means 18. The handle-providing means 18 of the depicted scalpel 20 includes an elongated handle member 22 to which the elongated blade 24 is fixedly secured adjacent one end of the handle member 22 and further includes a blade shield 26 which is joined to the handle member 22 for pivotal movement of the shield 26 between a first condition, as illustrated in FIGS. 1-4, at which the shield 26 covers the cutting edge of the blade 24 and a second condition, as illustrated in FIG. 5, at which the shield 26 is moved to an out-of-the-way position against the underside (as viewed in FIGS. 1-5) of the handle member 22 so that the cutting edge of the blade 24 is exposed for use.

The invention described herein can be embodied in both reusable or disposable scalpels. Accordingly, the principles of the present invention can be variously applied.

The scalpel 20 further includes a manually-operable, or a finger-depressible, actuator mechanism 30 which is pivotally joined to the handle member 22 for movement between a raised (or first) condition, as illustrated in FIG. 3, and a fully-depressed (or second) condition, as illustrated in FIG. 5, and a plurality of components, described herein, for moving the shield 26 from its first, or FIG. 3 blade-covering, condition to its second, or FIG. 5 out-of-the-way, condition upon depression of the actuator mechanism 30 from its FIG. 3 raised condition to its FIG. 5 fully-depressed condition. Additional componentry (described herein) of the scalpel 20 enables the actuator mechanism 30 to be releasably locked in its FIG. 5 fully-depressed condition and automatically return the actuator mechanism 30 to its FIG. 3 raised condition and automatically return the shield 26 to its FIG. 3 blade-covering condition when the actuator mechanism 30 is unlocked (and thereby released) from its fully-depressed FIG. 5 condition.

With reference to FIGS. 3-6, the handle member 22 includes an elongated body 32 having opposite front and rear ends 34 and 36, respectively, and defines two opposite side surfaces 38 and 40. The handle member 22 is relatively thin as measured between its opposite side surfaces 38 and 40 and includes a forwardly-extending blade support 28 to which the blade 24 is rigidly secured. Inasmuch as the scalpel 20 is intended to be grasped by an operator, or user, as the handle member 22 rests atop of the web of the hand which extends between the thumb and index finger of the grasping hand and the tips of the index finger and thumb of the grasping hand are positioned against the side surfaces 38 and 40 of the handle member 22 during use, it is preferred that the side surfaces 38 and 40 are provided with a plurality of circular recesses 42 disposed thereacross to both reduce the likelihood that the scalpel 20 will slip in any direction relative to the grasping hand during a surgical, or cutting, procedure and facilitate the manipulation of the handle member 22 during a cutting process performed with the scalpel 20. In this connection, the circular recesses 42 are sized to accept the tips of the fingers or thumbs of the operator's hand used to grasp the handle member 20 to reduce slip between the handle member 22 and the operator's hand while permitting the handle member 22 to be pivoted, as necessary, about the tips of the fingers and thumb of the grasping hand to alter the angular orientation of the handle member 22 during a cutting process.

In addition and as will be described herein, the body 32 of the handle member 22 is provided with a plurality of through-openings, post portions and other formations which facilitate the attachment of other scalpel componentry to the handle member 22. In this regard, the body 32 of the handle member 22 defines an elongated groove 31 (best shown in FIG. 6) in its upper surface which extends along at least a portion of a segment of the handle member body 32 and a pair of through-slots 33, 35 disposed along each side of the groove 31 which extend, or communicate, between the interior of the groove 31 and the side surfaces 38 and 40. In addition, the rearward-most end of the elongated groove 31 terminates at an abutment surface 37 whose purpose will be apparent herein.

Figure 6:
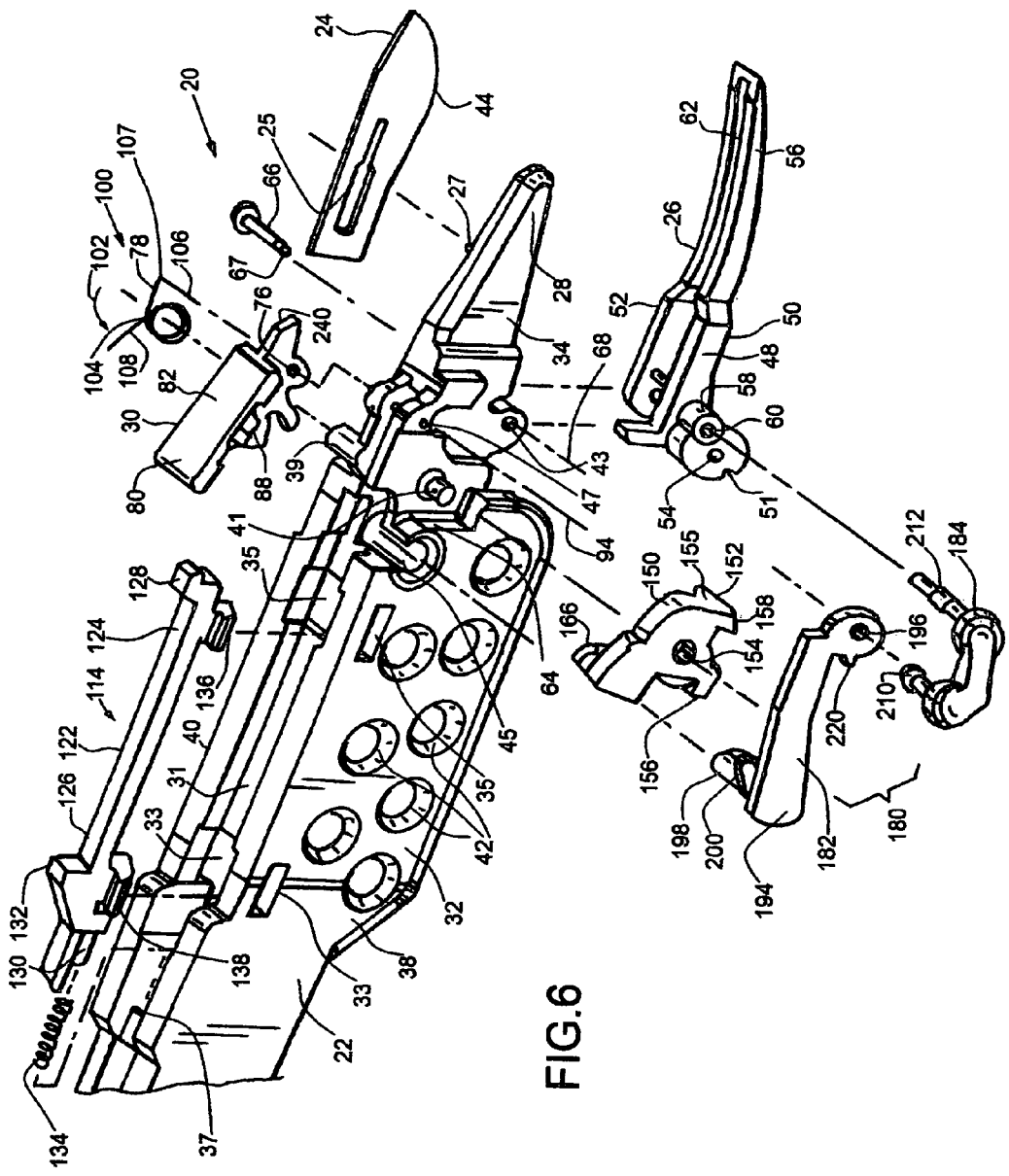
FIG. 6 is a perspective view of a fragment of the scalpel assembly of FIG. 1, shown exploded.

With reference still to FIG. 6, the front end 34 of the body 32 of the handle member 22 includes a first post portion 39 which extends away from the side of the handle member 22 which defines the side surface 40 and a second post portion 41 which extends away from the side of the handle member 22 which defines the side surface 38. Moreover, the front end 34 is provided with a circular recess 45 which opens out of the side surface 38, a transversely-extending through-opening 43 with which the blade shield 26 is connected to the handle member 22 and a transversely-extending through-opening 47 (of relatively small diameter) with which the actuator member 30 is secured to the handle member 22. In addition, the front end 34 of the body 32 defines a forwardly-facing abutment surface 64 disposed rearwardly of the post portion 41 whose purpose will be apparent herein. If the scalpel handle 18 is not intended to be reused, the body 32 of the handle member 22 is preferably formed in one piece out of a hard plastic material, but other materials can be used. In the alternative and if the scalpel handle 18 is intended to be reused, the handle member 22 is preferably constructed out of metal, such as stainless steel.

As best shown in FIG. 6, the blade 24 of the scalpel 20 is elongated and relatively thin in shape and defines a relatively sharp cutting edge 44 which extends along one (i.e. the lower edge as viewed in FIG. 6) of its edges. As is the case with common scalpel blades, the blade 24 defines an elongated slot 25 which is disposed medially of and extends along the blade body which enables the blade 24 to be secured to the blade support 28. To this end and for purposes of holding a replaceable blade 24, the blade support 28 (FIG. 6) is fashioned with a fitting 27 which is adapted to cooperate with the blade 24 in a manner which is well-known in the art to releasably attach the blade 24 to the blade support 28. Suffice it to say that in order to secure the blade 24 to the support 28, the blade 24 is positioned against the blade support 28 so that the elongated slot 25 accepts the fitting 27 of the support 28 and so that the blade 24 is thereby rigidly secured to the handle member 22. If the scalpel handle 22 is constructed of plastic and not intended to be reused (i.e. intended to be discarded with the blade following its initial use), the slot 25 of the blade 24 could be first positioned about the fitting 27, and the fitting 27 can be subsequently heated to heat seal the blade 24 in place. The blade 24 is preferably constructed of metal, such as stainless steel, but other materials can be used.

With reference to FIGS. 6 and 7, the blade shield 26 includes a body 46 having a bifurcated proximal portion 48 having a pair of prongs 50, 52 through which is defined a through-opening 54 with which the shield 26 is pivotally connected to the handle member 22 and further has an elongated distal portion 56 which extends from the proximal portion 48. One prong 50 of the proximal portion 48 also includes a boss 58 which is spaced radially from the through-opening 54 and defines a through-bore 60 whose purpose will be apparent herein. Meanwhile, the distal portion 56 is somewhat arcuate in shape as a path is traced along the length thereof and defines a blade-accepting groove 62 which extends therealong. The groove 62 is provided with a bottom whose shape is substantially complementary to the curvature of the blade cutting edge 44 so that when the shield 26 is positioned in its FIG. 3 blade-covering condition, the groove 62 accepts, and thereby covers, the blade cutting edge 44. Furthermore, there is provided within the prong 50 of the proximal portion 48 a finger portion 49 which extends substantially radially of the through-opening 54 and is provided with a tangentially-directed surface 72 adjacent the (free) end of the finger portion 49. In addition, a V-shaped notch 51 is formed in the proximal portion 48 so as to open radially of the through-opening 54. As will be apparent herein, the finger portion 49 is used to hold the blade shield 26 in its FIG. 3 (or FIG. 14) blade-covering condition, and the notch 51 is used to hold the blade shield in its FIG. 5 out-of-the-way condition.

To pivotally secure the shield 26 to the handle member 22, the prongs 50, 52 of the proximal portion 48 are positioned about the body 32 of the handle member 22 adjacent the front end 34 thereof so that the through-opening 54 is aligned with the through-opening 43 (FIG. 6) of the handle member 22, and then a pivot pin 66 is inserted through and secured within the aligned openings 54 and 43. If desired, the pin 66 can be molded so that its shank is provided with an enlarged end portion 67 so that when the pin 66 is inserted enlarged end portion-first through the aligned openings 54 and 43, the pin 66 is secured through the openings 54 and 43 in a snap-fit relationship therein.

It will be understood that with the blade shield 26 being pivotally secured to the handle member 22 as aforedescribed by way of the pivot pin 66, the shield 26 can be pivoted between the condition illustrated in FIG. 3 at which the distal portion 56 of the blade shield 26 extends forwardly of the handle member 22 and the cutting edge 44 of the blade 24 is accepted by the groove 62 of the distal portion 56 and the condition illustrated in FIG. 5 (and FIG. 16) at which the distal portion 56 extends rearwardly of the front end 34 of the handle member 22 so that the distal portion 56 is disposed remote of the cutting edge 44. In other words, when the shield 26 is positioned in its FIG. 5 out-of-the-way condition, the distal portion 56 is positioned against the underside of the handle member 22, and the cutting edge 44 of the blade 24 is exposed for use of the scalpel 20. In order that the distal portion 50 be substantially hidden from view when positioned in its FIG. 5 condition, the underside of the handle member 22 has been provided with a shield-accepting groove 61 (best shown in FIGS. 17, 18 and 19) having an arcuate surface 63 against which the distal portion 56 is adapted to rest. It will also be understood that the axis of pivot, indicated 68 in FIGS. 3-5, about which the shield 26 is pivotally moved between its FIG. 3 and FIG. 5 conditions is oriented substantially normal to the longitudinal axis of the handle member 22, and as the shield 26 is moved between its FIG. 3 and FIG. 5 positions, the shield 26 moves through about 180 degrees of movement.

As best shown in FIG. 8, the manually-operable actuator mechanism 30 of the scalpel assembly 20 includes an elongated body 74 having a connection portion through which a through-opening 76 is defined and with which the actuator mechanism 30 is pivotally connected to the body 32 of the handle member 22. To this end and with reference again to FIG. 6, the actuator mechanism 30 is positioned atop the handle member 22 so that the through-opening 76 is aligned with the through-opening 47 provided in the body 32 of the handle member 22, and the end of a torsion spring 78 (FIG. 6) is inserted through the aligned through-openings 76 and 47 to pivotally secure the actuator mechanism 30 to the handle member 22. The body 74 of the actuator mechanism 30 also includes a finger-depressible end having a platform portion 80 whose upper surface 82 is substantially normal to the longitudinal axis of the through-opening 76. Preferably, the upper surface 82 is bordered by a rim which enhances the frictional grip between the upper surface 80 and a finger with which the upper surface 82 is intended to be depressed.

The actuator mechanism 30 further includes a depending portion 84 situated beneath the underside, as viewed in FIG. 8, of the platform portion 80. The depending portion 84 defines a C-shaped notch 86 which opens somewhat rearwardly of the handle member 22 when the actuator mechanism 30 is secured to the handle member 22 by way of the torsion spring 78 (FIG. 6), and the depending portion 84 further includes a downwardly-directed boss 87 defining a cam surface 88 disposed along the underside thereof and additional cam surfaces 224 (FIG. 17*a*) and 225 (FIG. 18*a*) associated with the interior of the notch 86 whose purpose will be apparent herein.

It will be understood that with the manually-operable actuator mechanism 30 pinned, and thereby connected, to the handle member 22 by way of the torsion spring 78, the body 74 of the actuator mechanism 30 can be pivotally moved with respect to the handle member 22 between a raised condition, as illustrated in FIG. 3, and a fully-depressed condition, as illustrated in FIG. 5. As the actuator mechanism 30 is moved between its FIG. 3 and FIG. 5 conditions, its axis of pivot, indicated 94 in FIGS. 17, 18 and 19, relative to the handle body 32 is substantially normal to the longitudinal axis of the handle member body 32 and the path of movement of the actuator mechanism 30 relative to the handle member body 32 is substantially contained in a plane which contains the longitudinal axis of the handle member body 32.

The scalpel 20 also includes biasing means, generally indicated 100 in FIG. 6, for biasing the actuator mechanism 30 from the FIG. 5 fully-depressed condition toward the FIG. 3 raised condition. Within the depicted scalpel 20 and with reference to FIGS. 6 and 9, the biasing means 100 is the torsion spring 78, introduced earlier, having a coiled mid-portion 104 and a crooked leg portion 106 (having a straight portion 107) and an elongated portion 108 which are joined at opposite ends of the coiled mid-portion 104. To secure the torsion spring 102 in place within the scalpel 20, the actuator member 30 is positioned against the handle member 22 so that the through-opening 76 of the actuator member 30 is aligned with the through-opening 47 of the handle member 22 and the coiled mid-portion 104 is directed over the first post portion 39 (FIG. 6) of the handle member 22 while the straight portion 107 of the crooked leg portion 106 is simultaneously directed through the aligned through-openings 76 and 47. The elongated portion 108 of the spring 78 is then moved (about the post portion 39 in the direction indicated by the FIG. 6 arrow 102 in opposition to the biasing force of the coiled mid-portion 104) and manipulated into position against the underside of the platform portion 80 of the actuator mechanism 30. Preferably, the underside of the platform portion 80 is provided with an elongated groove 110 (FIG. 8) for accepting, and thereby retaining, the elongated portion 108 in place as it bears against the underside of the platform portion 80. With the elongated attachment portion 108 bearing against the underside of the platform portion 80 and the crooked leg portion 106 retainably positioned within the aligned through-openings 76 and 47, the torsion spring 78 acts between the handle member body 32 and the platform portion 80 to thereby urge the actuator mechanism 30 about the pivot axis 94 (FIGS. 17, 18 and 19) from the FIG. 5 fully-depressed condition toward the FIG. 3 raised condition at which the forward end portion 240 (FIG. 6) of the actuator mechanism 30 abuts (and thereby rests against) the upper surface of the handle member 22.

It is also a feature of the scalpel 20 that it includes means, generally indicated 114 in FIGS. 6, 18 and 19, for releasably locking the actuator mechanism 30 in its FIG. 5 fully-depressed condition. To this end, the depending portion 84 of the actuator member 30 includes a rearwardly-facing notch 112 (best shown in FIG. 8) disposed directly beneath the platform portion 80, and the scalpel 20 includes a spring-biased actuator latch mechanism 122 (best shown in FIG. 10) which is accepted by the groove 31 (FIGS. 6, 17, 18 and 19) for sliding movement therealong between first and second limits of travel. To this end and with reference again to FIG. 10, the latch mechanism 122 is in the form of an elongated shank member having two opposite forward and rearward end portions 124 and 126, respectively, and there is provided at the forward end 124 a forwardly-extending tab 128 which is adapted to be accepted by the rearwardly-facing notch 112 (FIG. 8) provided in the depending portion 84 of the actuator mechanism 30. In addition, there is provided at the rearward portion 126 of the latch mechanism 122 a rearwardly-directed post 130 and an upwardly-extending tab 132. An elongated compression spring 134 (FIGS. 6 and 17) is positioned about the post 130, and the latch mechanism 122 is positioned within the groove 31 (FIG. 6) so that the spring 134 abuts the abutment surface 37 of the groove 31 and is thereby adapted to act between the abutment surface 37 of the groove 31 and the rearward end portion 126 of the latch mechanism 122 so that the latch mechanism 122 is spring-biased forwardly along the groove 31 of the handle member body 32.

The latch mechanism 122 is permitted to slidably move relative to and along the length of the groove 31 between a first, or forward, limit of travel, as shown in FIG. 19, at which the forwardly-extending tab 128 is accepted by the rearwardly-facing notch 112 of the actuator mechanism 30 and a second, or rearward limit of travel at which the latch mechanism 122 has been forcibly urged (against the force of the compression spring 134) rearwardly along the groove 31 until the forwardly-extending tab 128 is fully withdrawn from the notch 112. It therefore follows that the latch mechanism 122 is urged by the compression spring 134 from its second, or rearward, limit of travel toward its first, or forward, limit of travel.

Figure 19A:
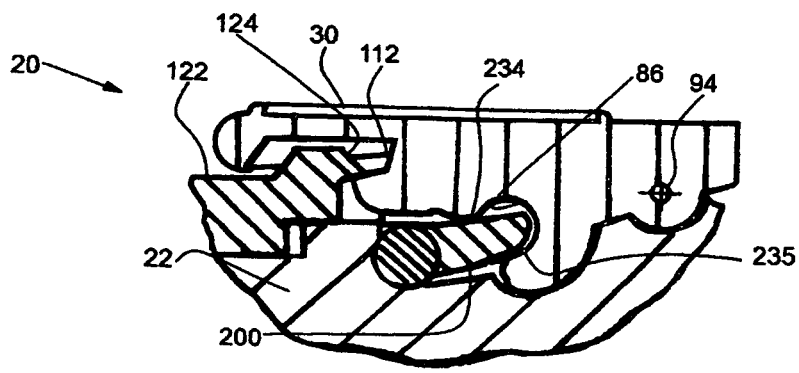
FIG. 19a is an enlarged view of the fragment of the FIG. 1 scalpel assembly shown in the circle F of FIG. 19.

As the actuator mechanism 30 is depressed from its FIG. 1 raised condition, the base, indicated 116 in FIG. 8, of the depending portion 84 is permitted to slide along the forward edge of the forwardly-extending tab 128 so that the latch mechanism 122 is urged rearwardly along the groove 31. When the actuator mechanism 30 reaches its FIG. 5 fully-depressed condition—at which point the opening of the notch 112 is positioned in operative registry (i.e. becomes aligned with) the tab 128 of the latch mechanism 122, the tab 128 is urged, under the influence of the spring 134, into the notch 112 (as best illustrated in FIGS. 19 and 19a) to thereby releasably secure the actuator mechanism 30 in its FIG. 5 fully-depressed condition.

To release the actuator mechanism 30 from its FIG. 5 locked, fully-depressed condition, the latch mechanism 122 is forcibly urged rearward against the force of the spring 134 to withdraw the tab 128 from the notch 112 so that the actuator mechanism 30 is thereafter permitted to return to its FIG. 3 raised condition under the influence of the torsion spring 78 (FIG. 6). The upwardly-extending tab 132 provided along the length of the latch mechanism 122 provides an operator with a convenient means, or surface, against which the operator can urge the latch mechanism 122 rearwardly of the groove 31 with, for example, a finger (e.g. the index finger) of the grasping hand for the purpose of releasing the actuator mechanism 30 from its locked, fully-depressed condition.

With reference again to FIGS. 6 and 10, the latch mechanism 122 is also provided with two pairs of tabs 136, 138 which project from the sides thereof and which are accepted by the corresponding pairs of slots 33, 35 (FIG. 6) provided along the sides of the groove 31. These tabs 136, 138 are resilient in nature and are appropriately located with respect to the through-slots 33, 35 so that when the latch mechanism 122 is manipulated into place within the groove 31, the tabs 136, 138 are accepted by the through-slots 33, 35 in a snap-fit relationship therewith and so that the latch mechanism 122 is releasably held within the groove 31 by the tabs 136, 138. It will also be understood that each of the through-slots 33, is provided with a length sufficient to accommodate the sliding movement of the latch mechanism 122 between the aforedescribed forward and rearward limits of travel along the groove 31.

As will be apparent herein, the biasing force of the torsion spring 78 exerted against the actuator mechanism 30 holds the blade shield 26 in its FIG. 3 (and FIG. 17) blade-covering condition until the platform portion 80 of the actuator mechanism 30 is depressed by a finger (i.e. the index finger) of the operator. Furthermore, once the actuator mechanism 30 has been unlocked from its FIG. 5 (and FIG. 19) fully-depressed condition (by withdrawing the tab 128 of the latch mechanism 122 from the notch 112), the actuator mechanism 30 is automatically returned to its FIG. 3 raised condition by the torsion spring 78. In connection with the foregoing, there is situated between the actuator mechanism 30 and the blade shield 26 an arrangement of components, described herein, which effect the movement of the blade shield 26 from its FIG. 3 (and FIG. 17) blade-coving condition to its FIG. 5 (and FIG. 19) out-of-the-way, or blade-exposing, condition as the actuator mechanism 30 is depressed and which also effects the return of the blade shield 26 from its FIG. 3 (and FIG. 17) blade-exposing condition to its FIG. 5 (and FIG. 19) out-of-the-way condition upon release of the actuator mechanism 30 from its FIG. 5 (and FIG. 19) fully-depressed condition.

With reference to FIG. 11, the aforementioned arrangement of components situated between the actuator mechanism 30 and the blade shield 26 includes a shield latch mechanism 150 which is disposed between the actuator mechanism 30 and the blade shield 26 which, in use, releasably locks the shield 26 in its FIG. 3 blade-covering condition and cooperates with the actuator mechanism 30 so that when the actuator mechanism 30 is depressed from its FIG. 3 raised condition, the shield latch mechanism 150 releases the blade shield 26 from its FIG. 3 blade-covering condition. In this connection and as illustrated in FIGS. 6, 11 and 14-16, the shield latch mechanism 150 includes a substantially platen-like body 152 having a through-bore 154 with which the body 152 is pivotally joined to the handle member body 32. To this end, the shield latch mechanism 150 is arranged against the handle member body 32 by directing the through-bore 154 of the latch mechanism body 152 over the post portion 41 (FIG. 6) of the handle member 22. It follows that when positioned about the post portion 41, the shield latch mechanism 150 is capable of pivoting relative to the handle member 22 between alternative angular positions (described herein).

The body 152 of the shield latch mechanism 150 includes a forward portion 155 disposed forwardly of the through-bore 154 and an opposite rearward portion 156. As best shown in FIGS. 6 and 11, the forward portion 155 is provided with a shape along its periphery so as to provide a hook-providing shoulder 158 which is capable of being hooked about the tip of the finger portion 49 (FIGS. 7 and 14) of the blade shield body 46 for releasably locking the blade shield 26 in its FIG. 3 blade-covering condition. Meanwhile, the rearward portion 156 of the shield latch mechanism 150 is shaped so as to provide an arcuate-shaped cam surface 166 (along its uppermost portion) which is capable of being cooperatively engaged by the cam surface 88 (FIG. 8) defined along the boss 87 of the depending portion 84 of the actuator mechanism 30 as will be described herein. Furthermore, the rearward portion 156 (FIG. 11) is provided with a rearwardly-opening cutout 168 having a bottom 169, and a small leaf spring 170 is secured against the bottom 169 of the cutout 168. More specifically and as best shown in FIG. 11, the leaf spring 170 has two opposite ends 172, 174 and an arcuate mid-portion 176 which extends between the spring ends 172, 174, and it is (at least one of) the spring ends 172, 174 which are glued (or otherwise secured) against the bottom 169 of the cutout 168 to hold the spring 170 within the cutout 168. When the shield latch 150 is mounted upon the handle member body 32 (i.e. positioned about the post portion 41 thereof), the forward portion 155 of the shield latch body 152 is disposed forwardly of the post portion 41, the cam surface 166 is disposed directly beneath the cam surface 88 (FIG. 6) of the actuator member 30, and the mid-portion 176 of the leaf spring 170 is positioned so as to engage (and act against) the abutment surface 64 of the handle member body 32, as best shown in FIGS. 14-16.

With the shield latch mechanism 150 positioned about the post portion 41 of the handle member body 32 as aforedescribed, the leaf spring 170 continually biases the shield latch mechanism 150 in one rotational, or pivotal, direction about the post portion 41 toward one condition, as illustrated in FIG. 14, at which the hook-providing shoulder 158 is hooked about the tip of the finger portion 49 of the blade shield 26—and thus releasably lock the blade shield 26 in its FIG. 3 blade-covering condition, from another condition, as illustrated in FIG. 15, at which the hook-providing shoulder 158 is elevated above, so as to clear, the tip of the finger portion 49 of the blade shield 26—and thereby release the blade shield 26 from its FIG. 3 locked, blade-covering condition. In other words, the leaf spring 170 continually urges the shield latch 150 to rotate, or pivot, in a clockwise direction (as viewed in FIGS. 14 and 15) about the post portion 41 from the aforedescribed another (i.e. FIG. 15) condition toward the aforedescribed one (i.e. FIG. 14) condition.

As mentioned above, the hook-providing shoulder 158 of the shield latch 150 is adapted to hook about the tip of the finger portion 49 of the blade shield body 46 to thereby releasably lock the blade shield 26 in its FIG. 3 blade-covering condition. Accordingly, the shield latch 150 is disposed in such a relationship to the blade shield 26 so then when the blade shield 26 is positioned in its FIG. 3 blade-covering condition and the shield latch mechanism 150 is positioned in its one (FIG. 14) condition with respect to the handle member body 32, the hook-providing shoulder 158 is hooked about the tip of the finger portion 49. Therefore and when the shield latch 150 is subsequently moved to its another (FIG. 15) condition with respect to the handle member body 22 (and against the biasing force of the leaf spring 170), the hook-providing shoulder 158 of the latch mechanism 150 is positioned above so as to clear the tip of the finger portion 49 and thereby release the blade shield 26 from its FIG. 3 locked, blade-covering condition.

In addition and as mentioned earlier, the cam surface 88 (FIG. 6) of the actuator mechanism 30 is engageable with the cam surface 166 (FIG. 11) provided along the rearward portion 156 of the shield latch body 152, and these engageable cam surfaces 88 and 166 are shaped so that when the actuator mechanism 30 is depressed from its FIG. 3 raised condition toward its FIG. 5 fully-depressed condition, the cam surface 88 moves downwardly against the cam surface 166 so that the shield latch mechanism 150 is forced to rotate or pivot (e.g. counter-clockwise as viewed in FIG. 14) from the depicted FIG. 14 condition toward the depicted FIG. 15 condition and against the biasing force of the leaf spring 170 and so that the shield latch mechanism 150 (by way of the hook-providing shoulder 158) releases the blade shield 26 from its FIG. 5 blade-covering condition. As will be apparent herein and within the depicted scalpel 20, it is during a first phase of movement of the actuator mechanism 30 from its FIG. 3 raised condition toward its FIG. 5 fully-depressed condition that the shield latch mechanism 150 releases the tip of the finger portion 49 and thus releases the blade shield 26 from its locked, blade-covering condition of FIG. 14.

With reference again to FIG. 6, the scalpel 20 further includes a linkage assembly, generally indicated 180, with which the downwardly-directed movement of the actuator member 30 from the FIG. 3 raised condition to the FIG. 5 fully-depressed condition is transmitted to the blade shield 26 so that the blade shield 26 is rotated about the FIG. 6 pivot pin 66 (i.e. the pivot axis 68 of FIGS. 17, 18 and 19) from the FIG. 3 blade-covering condition to the FIG. 5 out-of-the-way condition. Within the depicted scalpel 20, the linkage assembly 180 includes a lever arm 182 (FIGS. 6 and 13) and a linkage element 184 (FIGS. 6 and 12) which are joined to one another and between the actuator member 30 and the blade shield 26 so that upon movement of the actuator mechanism 30 downwardly from the position at which the shield latch mechanism 150 is released by the hook-providing shoulder 158, the actuator mechanism 30 urges the lever arm 182 to move in a manner described herein which, in turn, effects a desired movement of the linkage element 184 which, in turn, effects the desired rotation of the blade shield 26 from its FIG. 3 blade-covering condition to its FIG. 5 out-of-the-way condition.

Figure 13:
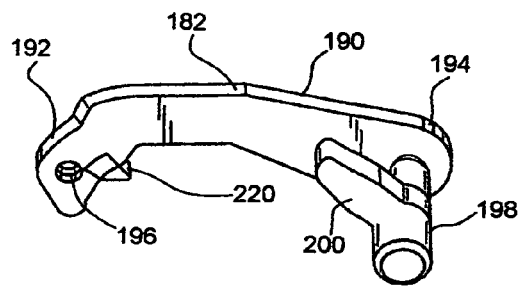
FIG. 13 is a perspective view of a lever arm of the linkage assembly of the FIG. 1 scalpel assembly.

With regard to the foregoing and as best shown in FIG. 13, the lever arm 182 includes an elongated body 190 having two opposite ends 192 and 194, and one end 192 of the lever arm 182 defines a through-opening 196 with which the linkage element 184 is pivotally connected to the lever arm 182, as will be explained herein. The body 190 of the lever arm 182 includes a post portion 198 situated adjacent the end 194 of the body 190 opposite the end 192 so as to extend substantially normal to the longitudinal axis of the body 190 and a finger portion 200 which extends radially from the post portion 198. The lever arm 182 is pivotally attached to the handle member body 32 by way of the post portion 198 as the post portion 198 is directed endwise into the circular recess 45 (FIG. 6) which opens from one side surface 38 of the handle member body 32. With the post portion 182 positioned within the circular recess 45 in this manner, the end 192 of the lever arm 182 is capable of being pivoted about the circular recess 45 (i.e. the pivot axis 201 of FIGS. 14-16), and thus relative to the handle member 22, between a first condition, as illustrated in FIGS. 3 and 4, at which the end 192 of the lever arm 182 is in an elevated condition and a second condition, as illustrated in FIG. 5, at which the end 192 has dropped (from the position illustrated in FIGS. 3 and 4) to a lowered condition.

Figure 12:
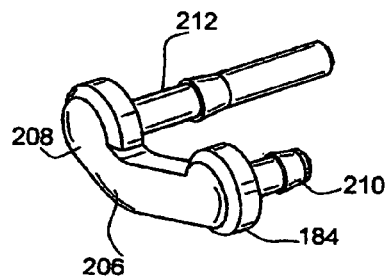
FIG. 12 is a perspective view of a linkage element of the linkage assembly of the FIG. 1 scalpel assembly.

Meanwhile and with reference to FIG. 12, the linkage element 184 includes a body 206 which is formed somewhat in the shape of a U having a base portion 208 and a pair of parallel pin portions 210 and 212 which extend from the base portion 208 and thereby provide the legs of the U shape of the linkage element body 206. With reference again to FIG. 6, the linkage element 184 is pivotally joined to both the lever arm 182 and the blade shield 26 as the pin portion 210 is positioned and secured within the through-opening 196 of the lever arm 182 and as the pin portion 212 is positioned and secured within the through-bore 60 defined within the proximal portion 48 of the blade shield 26. Preferably, each of the ends of the pin portions 210 and 212 are slightly enlarged in size to accommodate a snap-fit relationship within the through-opening 196 or through-bore 60 when positioned therein.

With the end 194 of the lever arm 182 anchored to (i.e. pivotally mounted upon) the handle member 22 by way of the circular recess 45 and the blade shield 26 anchored to (i.e. pivotally mounted upon) the handle member 22 by way of the pivot pin 66, movement of the actuator mechanism 30 between the raised condition of FIG. 3 and the fully-depressed condition of FIG. 5 forces the lever member 182 and linkage element 184 to operate as a two-bar linkage assembly whose paths of movement are fixed according to the location to which the lever member 182 and linkage element 184 are connected to one another and to the blade shield 26. Within the depicted scalpel 20, the location of the pivot axis, indicated 204 in FIG. 14, about which linkage element 194 is permitted to pivot relative to the lever arm 182 (by way of the pin portion 210) and the location of the pivot axis, indicated 206 in FIG. 14, about which the blade shield 26 is permitted to pivot relative to the linkage element 194 (by way of the pin portion 212) have been predetermined so that as the end 192 of the lever arm 182 is pivoted about its post portion 198 (i.e. the pivot axis 201) between the elevated condition of FIG. 3 and the lowered condition of FIG. 5, the linkage element 184 is forced to rotate the blade shield 26 through about 180 degrees of movement or, in other words, between the blade-covering condition of FIG. 3 and the out-of-the-way condition of FIG. 5. In connection with the foregoing and as best shown in FIG. 14, a first imaginary line which is drawn between the pivot axes 204 and 206 is spaced by a distance 214 (FIGS. 14 and 16) from a second imaginary line drawn parallel to the first imaginary line which intersects the pivot axis 68.

When the scalpel 20 is used in a cutting, or surgical, operation, it is desirable that the blade shield 26 be maintained in a relatively secure condition against the underside (i.e. the arcuate groove surface 63 of FIGS. 17, 18 and 19) of the handle member 22. With this in mind and to prevent the blade shield 26 (or, more specifically, the distal portion 56 of the blade shield 26) from unintentionally falling downwardly from its position against the groove surface 63 of the handle member 22, one end 192 of the lever arm 182 is provided with a V-shaped hook portion 220 (FIGS. 6 and 13) which is accepted by the V-shaped notch 51 defined in the proximal portion 48 of the blade shield 26 when the blade shield 26 is positioned in its FIG. 5 out-of-the-way condition, as best shown in FIG. 5. As long as the end 192 of the lever arm 194 is positioned within its FIG. 5 lowered condition, the hook portion 220 and notch 51 cooperate to prevent the blade shield 26 from dislodging or inadvertently falling from its position against the groove surface 63 of the handle member 22 when the shield 26 is positioned in its FIG. 5 out-of-the-way condition.

It is a feature of the scalpel 20 that the end 192 of the lever arm 182 is forcibly moved downwardly from the raised condition of FIG. 3 to the lowered condition of FIG. 5 to thereby move the blade shield 26 from the blade-covering condition of FIG. 3 to the out-of-the-way condition of FIG. 5 upon movement of the actuator mechanism 30 from its FIG. 3 raised condition to the FIG. 5 fully-depressed condition. To this end and with reference to FIGS. 17-19 and 17a-19a, the actuator mechanism 30 and the finger portion 200 define a first set of engageable cam surfaces (described herein) which cooperate in such a fashion so that the manual depression of the platform portion 80 of the actuator mechanism 30 from the FIG. 3 raised condition to the FIG. 5 fully-depressed condition urges the lever arm end 192 downwardly as aforedescribed. Furthermore, the actuator mechanism 30 and the finger portion 200 define a second set of engageable cam surfaces (described herein) which cooperate in such a fashion so that upon return of the platform portion 80 of the actuator mechanism 80 from the FIG. 5 fully-depressed condition toward the FIG. 3 raised condition, the finger portion 200, and thus the lever arm end 192, is returned upwardly from its FIG. 19 lowered condition to its FIG. 17 raised condition.

Figure 17A:
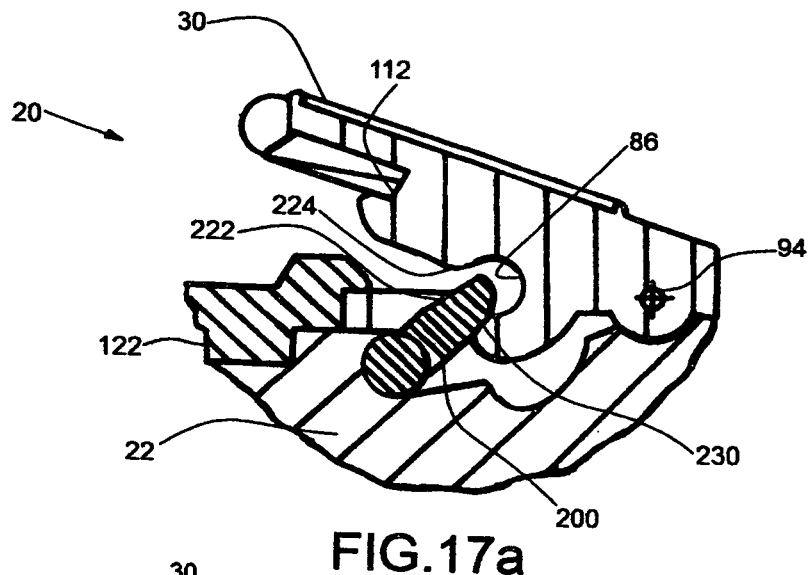
FIG. 17a is an enlarged view of the fragment of the FIG. 1 scalpel assembly shown in the circle D of FIG. 17.
Figure 18A:
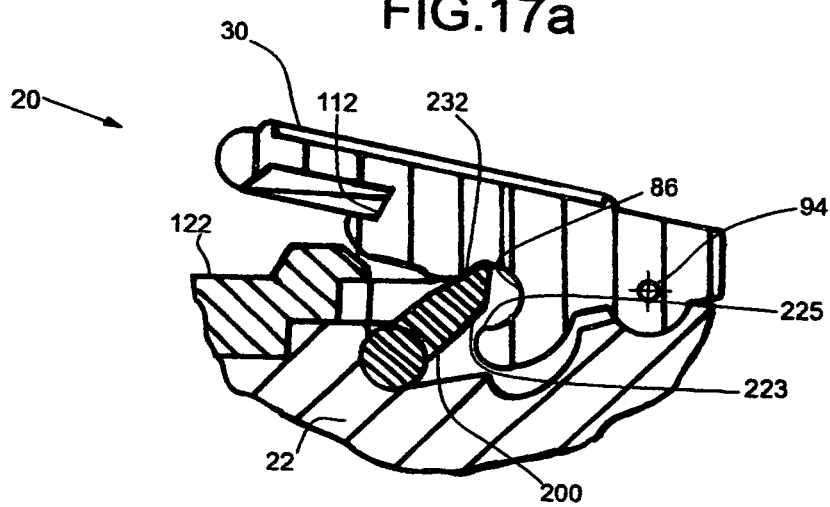
FIG. 18a is an enlarged view of the fragment of the FIG. 1 scalpel assembly shown in the circle E of FIG. 18.

In connection with the foregoing and as best shown in FIGS. 17a, 18a and 19a, the tip of the finger portion 200 is accepted, or captured, by the notch 86 defined in the depending portion 84 of the actuator mechanism 30, and the tip of the finger portion 200 remains captured by the notch 86 throughout the movement of the actuator mechanism 30 between its FIG. 3 raised condition and its FIG. 5 fully-depressed condition. Furthermore, the aforementioned first set of cam surfaces include a cam surface 222 (FIG. 17a) which is defined along the upper surface (as viewed in FIG. 17a) of the finger portion 200 and a cam surface 224 (introduced earlier) which is defined along the upper edges of the notch 86, and the aforementioned second set of cam surfaces include a cam surface 223 (FIG. 18a) which is defined along the lower surface (or underside) of the finger portion 200 and a cam surface 225 (introduced earlier) which is defined along the lower edges of the notch 86. When the actuator mechanism 30 is positioned in its FIG. 17 (and FIG. 17a) raised condition—as would be the case before the actuator mechanism 30 is begun to be depressed toward its FIG. 19 (and FIG. 19a) fully-depressed condition, the cam surfaces 224 and 222 are spaced from one another.

As the actuator mechanism 30 is depressed from its FIG. 17 (and FIG. 17a) raised condition to the FIG. 18 (and FIG. 18a) partially-depressed condition, the notch cam surface 224 moves downwardly, as well, and engages the finger portion cam surface 222 at a contact point, indicated 232 in FIG. 18a. Meanwhile, the opening of the notch 86 is large enough so that between the moment that the cam surface 224 begins to move downwardly until the moment that the cam surface 224 engages the cam surface 222, the finger portion 200, and thus the lever arm 182 are not moved relative to the handle member 22. Therefore and through the first phase of downward movement of the actuator mechanism 30 toward its fully-depressed condition, the finger portion 200, and thus the lever arm 182, remains in a stationary condition in relation to the handle member 22 by virtue of the (relatively large) shape, or opening, of the notch 86. However and while the lever arm 182 remains stationary during this aforedescribed first phase of movement, the cam surface 166 (FIGS. 6 and 11) of the shield latch mechanism 150 is acted upon by the cam surface 88 (FIG. 8) of the actuator mechanism boss 87 to pivotally move the shield latch mechanism 150 to its FIG. 14 shield-locking condition to its FIG. 15 shield-release condition. Therefore and until the blade shield 26 is unlocked by the shield latch mechanism 150 (i.e. at the end of the first phase of downward movement of the actuator mechanism 30), the blade shield 26 is maintained in its blade-covering condition as depicted in each of the views of FIGS. 4, 15, 18 and 18a.

Continued movement of the actuator mechanism 30 downwardly from the FIG. 18 (and FIG. 18a) partially-depressed condition to the FIG. 19 (and FIG. 19a) fully-depressed condition moves the cam surface 224 of the notch 86 downwardly against (and into sliding movement along with) the cam surface 222 of the finger portion 200 from a contact point 232 (FIG. 18a) to a contact point 234 (FIG. 19a) to thereby forcibly move the lever arm 182 from its FIG. 18 raised condition to its FIG. 19 lowered condition and so that the blade shield 26 is forcibly moved by way of the linkage assembly 180 from the FIG. 18 blade-covering condition to the FIG. 19 out-of-the-way condition. It also follows that as the actuator mechanism 30 travels the full length of its movement from the FIG. 18 partially-depressed condition to the FIG. 19 fully-depressed condition, the cam surfaces 222 and 224 remain engaged with one another between the FIG. 18a contact point 232 and the FIG. 19a contact point 234. In addition and when the lever arm 184 has been moved downwardly to its FIG. 19 lowered position, the forward end portion 124 of the lever latch mechanism 122 is accepted by the rearwardly-facing notch 112 defined within the actuator mechanism 30 to thereby releasably hold the actuator mechanism 30 in its FIG. 19 (and FIG. 19a) fully-depressed condition.

Upon release of the actuator mechanism 30 from its FIG. 19 fully-depressed condition (by manually moving the lever latch mechanism 122 rearwardly along the handle member groove 31 to thereby withdraw the forward end portion 124 of the latch mechanism 122 from the actuator mechanism notch 112), the torsion spring 78 (FIGS. 6 and 9) is permitted to urge the actuator mechanism 30 upwardly from its FIG. 19 fully-depressed condition toward its FIG. 17 raised condition. As the actuator mechanism 30 is urged upwardly from the FIG. 19 fully-depressed condition, the cam surface 225 of the notch 86 moves upwardly against (and slides along) the cam surface 223 of the finger portion 200 (from an initial contact point, indicated 235 in FIG. 19a) to forcibly move the lever arm 182 from its FIG. 19 lowered condition to its FIG. 18 raised condition and so that the blade shield 26 is forcibly moved by way of the linkage assembly 180 from its FIG. 19 out-of-the-way condition to its FIG. 18 blade-covering condition. It also follows that as the actuator mechanism 30 travels the full length of its movement from the FIG. 19 fully-depressed condition to the FIG. 18 partially-depressed condition, the cam surfaces 223 and 225 remain engaged with one another between the FIG. 19a contact point 235 and a contact point, indicated 230 in FIG. 17a.

Continued movement of the actuator mechanism 30 upwardly from the FIG. 18 (and FIG. 18a) partially-depressed condition to the FIG. 17 (and FIG. 17a) raised condition permits the shield latch mechanism 150 to move, by way of the leaf spring 170, to pivot about the post portion 41 to its FIG. 14 shield-locking condition while the finger portion 200, and thus the lever arm 182, remains stationary with respect to the handle member 22. Therefore and whereas the downward movement of the actuator mechanism 30 from its raised condition toward its fully-depressed condition effects the movement of the blade shield 26 from its blade-covering condition to its out-of-the-way condition in a two-stage process of movement—the first of which unlocks the blade shield 26 from the blade shield latch mechanism 150 and the second of which bodily moves the blade shield 26 to its out-of-the-way condition, the upward movement of the actuator mechanism 30 from its fully-depressed condition to its raised condition returns the blade shield 26 to its blade-covering condition in a two-stage process of movement. That is to say, a first stage of upward movement of the actuator mechanism 30 effects the bodily movement of the blade shield 26 to its blade-covering condition and a second stage of upward movement of the actuator mechanism 30 permits the blade shield 26 (i.e. in its blade-covering condition) to be locked in place with the blade shield locking mechanism 150.

It also follows that whether the actuator mechanism 30 is moved upwardly or downwardly between its FIG. 17 (and FIG. 17a) raised condition and its FIG. 19 (and FIG. 19a) condition, the actuator mechanism 30 and the lever member 182 to act as cam and cam follower, respectively, since it is the downwardly-directed movement of the actuator mechanism 30 which effects the downward movement of the lever arm end 192 (by way of the finger portion 200) from the raised condition of FIGS. 3 and 4 to the lowered condition of FIG. 5 and it is the upwardly-directed movement of the actuator mechanism 30 which effects the upward movement of the lever arm end 192 (by way of the finger portion 200) from the lowered condition of FIG. 5 to the raised condition of FIGS. 3 and 4.

The operation of the scalpel 20 in order to move the blade shield 26 between its FIG. 3 blade-covering condition and its FIG. 5 out-of-the-way conditions can be summarized as follows:

Before the actuator mechanism 20 is depressed, the actuator mechanism 30 is held in its FIG. 3 raised condition by the torsion spring 78, the lever arm end 192 is held in its FIG. 3 elevated condition by the upwardly-directed urging of the cam surface 225 of the actuator mechanism 30 against the cam surface 223 of the finger portion 200, and the shield latch mechanism 150 is held in its FIG. 14 blade shield-locking condition by way of the leaf spring 170, and the blade shield 26 is held in its FIG. 3 blade covering condition by way of the hook-providing shoulder 158 of the shield latch mechanism 150. It will therefore be understood that it is the torsion spring 78 which both biases the actuator mechanism 30 to its FIG. 3 raised condition and biases the lever arm end 192 (by way of the action of the cam surface 225 against the cam surface 223) to the FIG. 14 shield-locking condition. As the actuator mechanism 30 is depressed manually (e.g. with the index finger of the operator's hand used to grasp the handle member 22 about the sides thereof) through its first phase of downward movement, the shield latch mechanism 150 is rotated (against the biasing force of the leaf spring 170) to its shield-release condition depicted in FIG. 15 by way of the action of the cam surface 88 against the cam surface 166.

As the actuator mechanism 30 continues to be depressed manually through its second phase of downward movement, the lever arm end 192 is rotated from its FIG. 3 (and 4) elevated condition toward its FIG. 5 lowered position by way of the action of the cam surface 224 (FIG. 17a) against the cam surface 222 of the finger portion 200 which, in turn, effects the movement (by way of the linkage element 184) of the blade shield 26 from its FIGS. 3 and 4 blade-covering condition to its FIG. 5 out-of-the-way condition. Upon movement of the blade shield 26 to its FIG. 5 out-of-the-way condition, the V-shaped hook portion 220 of the lever arm 182 is accepted by the V-shaped notch 51 to maintain the distal portion 56 of the blade shield 26 against the underside of the handle member 22.

As the actuator mechanism 30 is depressed downwardly from its FIG. 2 raised condition, the forwardly-extending tab 128 of the lever latch mechanism 122 is simultaneously urged rearwardly along the groove 31 of the handle member 22 as the depending portion 84 of the actuator mechanism 30 bears against the upper surface of the tab 128 and urges the latch mechanism 122 rearwardly along the groove 31. However and upon eventual movement of the actuator mechanism 30 downwardly to its FIG. 5 fully-depressed condition, the notch 112 is disposed in registry with the tab 128 so that the tab 128 is directed forwardly into the notch 112 by the compression spring 134 to thereby releasably secure the actuator mechanism 30 in its FIG. 5 fully-depressed condition (and as best shown in FIG. 19a) and thereby retain the blade shield 26 in its FIG. 5 out-of-the-way condition to enable the blade 24 of the scalpel 20 to be used by an operator. If desired, the underside of the tab 128 can be appropriately sloped, or chamferred, so that the biasing force of the spring 134 continually urges the actuator mechanism 30 downwardly from its FIG. 5 fully-depressed condition which, in turn, (and due to the cooperating engagement of the cam surface 224 against the cam surface 222 at contact point 234) spring-biases the V-shaped hook portion 220 of the lever arm 182 into the V-shaped notch 51 of the blade shield 26 to aid in the maintaining of the blade shield 26 against the groove surface 63 (FIG. 19) of the handle member 22.

To return the blade shield 26 from the FIG. 5 out-of-the-way condition to its FIG. 3 blade-covering condition, the lever latch mechanism 122 is manually slid rearwardly along the groove 31 of the handle member 22 so that the forwardly-extending tab 128 of the lever latch mechanism 122 is withdrawn from the notch 112 of the actuator mechanism 30 to thereby release the actuator mechanism 30 from its locked, fully-depressed condition of FIG. 19. Upon release of the actuator mechanism 30 from its locked, fully-depressed condition, the torsion spring 78 is permitted to return the actuator mechanism 30 to its FIG. 3 raised condition so that the cam surface 225 (FIG. 18a) of the notch 86 bears upwardly against the cam surface 223 of the finger portion 200 and so that the blade shield 26 is rotated about its pivot axis 68 to its FIG. 3 blade-covering condition. Furthermore and upon the release of the actuator mechanism 30 from its locked condition, the cam surface 88 of the actuator mechanism 30 ceases to exert downwardly-directed forces upon the cam surface 166 of the shield latch mechanism 150 so that the shield latch mechanism 150 is permitted to return (by way of the leaf spring 170) to its FIG. 14 shield-locking condition to complete the readiness of the scalpel 20 for any subsequent depression of the actuator mechanism 30 in order to move the blade shield 26 to its FIG. 5 out-of-the-way condition.

In an exemplary scalpel 20 and when the actuator mechanism 30 is disposed in its FIG. 3 raised condition, the various components of the scalpel 20 are provided with dimensions which enable the upper surface 82 of the platform portion 80 of the actuator mechanism 30 to form an angle 242 (FIG. 3) with the (e.g. horizontally-disposed) upper surface of the handle member 22 of about 18.8 degrees. Meanwhile, when the actuator mechanism 30 is disposed in its FIG. 4 partially-depressed condition, the upper surface 82 of the platform portion 80 forms an angle 244 (FIG. 4) with the (e.g. horizontally-disposed) upper surface of the handle member 22 of about 12.6 degrees. Upon depressing the actuator mechanism 30 to its FIG. 5 fully-depressed condition, the upper surface 82 of the platform portion 80 is substantially parallel with the (e.g. horizontally-disposed) upper surface of the handle member 22.

It follows from the foregoing that a scalpel handle-providing means (or handle) 18 has been described for holding a blade 24 having a cutting edge 44 which, includes a handle member 22 and a blade shield 26 for covering, when desired, the blade cutting edge 44. The blade shield 26 is connected to the handle member 22 for pivotal movement relative thereto about a pivot axis 68 between a blade-covering condition and an out-of-the-way condition, and a movable shield latch mechanism 150 is capable of releasably locking the blade shield 26 in its blade-covering condition. A finger-operable actuator mechanism 30 is mounted upon the handle member 22 for pivotal movement between a first (i.e. raised) condition and a second (i.e. fully-depressed) condition, and a torsion spring 78 is interposed between the actuator mechanism 30 and the blade shield 26 for biasing the actuator mechanism 30 from the second (i.e. fully-depressed) condition toward its first (i.e. raised) condition. During a first phase of movement of the actuator mechanism 30 from its first condition to its second condition, the shield latch mechanism 150 unlocks the blade shield 26 from its locked blade-covering condition, and during a second phase of movement of the actuator mechanism 30 from its first condition to its second condition, the blade shield 26 is moved from its blade-covering condition to its out-of-the-way condition.

It will be understood that numerous modifications and substitutions can be had to the aforedescribed embodiment 20 without departing from the spirit of the invention. Accordingly, the aforedescribed embodiment 20 is intended for the purpose of illustration and not as limitation.

The invention claimed is:

1. A scalpel handle for holding a blade having a cutting edge, the scalpel handle comprising:

a handle member to which a blade is securable for use;

a blade shield for covering the cutting edge of the blade when the blade is secured to the handle member wherein the blade shield is connected to the handle member for pivotal movement relative thereto between a blade-covering condition at which the blade shield covers the cutting edge of the blade and an out-of-the way condition at which the cutting edge of the blade is exposed for use;

a manually-operable actuator mechanism which is mounted upon the handle member for movement relative thereto between a first condition and a second condition; and a linkage assembly interposed between the actuator mechanism and the blade shield, and the actuator mechanism is adapted to cooperate with the linkage assembly so that by manually moving the actuator mechanism from the first condition toward the second condition, the blade shield is moved by way of the linkage assembly from its blade-covering condition toward its out-of-the-way condition; and a first biasing means for acting between the actuator mechanism and the handle member so that the actuator mechanism is continually biased from its second condition toward its first condition and so that manual movement of the actuator mechanism from the first condition toward the second condition moves the actuator mechanism against the force of the first biasing means;

means for releasably locking the actuator mechanism in its second condition wherein the means for releasably locking the actuator mechanism includes a movable member which is mounted upon the handle member for movement relative thereto between a locked condition at which the movable member is interlocked with the actuator mechanism when in its second condition for locking the actuator mechanism in its second condition and an unlocked condition at which the movable member is withdrawn from its interlocked relationship with the actuator mechanism; and a second biasing means for biasing the movable member from its unlocked condition toward its locked condition so that upon movement of the actuator mechanism into its second condition, the movable member is automatically moved, by way of the second biasing means, into its interlocked relationship with the actuator mechanism for locking the actuator mechanism in its second condition and thereby locking the blade shield in its out-of-the-way condition.

2. The scalpel handle as defined in claim 1 wherein the linkage assembly includes a lever arm which is connected to the handle member for pivotal movement with respect thereto between a first position which corresponds to the position of the blade shield when in its blade-covering condition and a second position which corresponds to the position of the blade shield when in its out-of-the-way condition, and the actuator mechanism and the lever arm cooperate with one another so that the return of the actuator member from the second condition toward the first condition by way of the first biasing means effects the movement of the blade shield from its out-of-the-way condition to its blade-covering condition.

3. The scalpel handle as defined in claim 1 further comprising a shield latch mechanism for releasably locking the blade shield in its blade-covering condition and being connected to the handle member for movement relative thereto between one condition at which the blade shield is releasably locked in its blade-covering condition and another condition at which the blade shield is released from its locked blade-covering condition; and wherein the actuator member is adapted to be moved through a first phase of movement and then through a second phase of movement as the actuator mechanism is moved from the first condition to the second condition; and the actuator mechanism is adapted to cooperate with the shield latch mechanism and the linkage assembly so that by manually moving the actuator mechanism through its first phase of movement from the first condition to the second condition, the shield latch mechanism is moved by the actuator mechanism from its one condition to its another condition and so that by manually moving the actuator mechanism through its second phase of movement from the first condition to the second condition, the blade shield is moved by way of the linkage assembly from the blade-covering condition to the out-of-the-way condition.

4. The scalpel handle as defined in claim 3 wherein the linkage assembly includes a lever arm which is connected to the handle member for pivotal movement with respect thereto between a first position which corresponds to the position of the blade shield when in its blade-covering condition and a second position which corresponds to the position of the blade shield when in its out-of-the-way condition, and the actuator mechanism and the lever arm cooperate with one another so that by permitting the actuator member to return from its second condition toward its first condition by way of the first biasing means effects the return of the blade shield from its out-of-the-way condition to its blade-covering condition.

5. The scalpel handle as defined in claim 4 wherein the linkage assembly further includes a linkage element having a portion which is pivotally joined to the lever arm and another portion which is pivotally joined to the blade shield so that as the actuator mechanism is moved through its second phase of movement from its first condition toward its second condition, the lever arm and linkage element act as a two-bar linkage assembly for transmitting the movement of the actuator mechanism to the blade shield.

6. The scalpel handle as defined in claim 5 wherein the lever arm includes a portion which is adapted to cooperatively interlock with the blade shield when the blade shield is positioned in its out-of-the-way condition so that as long as the lever arm portion is cooperatively interlocked with the blade shield, the blade shield is secured in its out-of-the-way condition.

7. The scalpel handle as defined in claim 1 wherein the movable member includes an elongated member which is mounted upon the handle member for sliding movement relative thereto between an extended condition at which the elongated member cooperatively interlocks with the actuator mechanism to secure the actuator mechanism in its second condition and a retracted condition at which the elongated member is withdrawn from its interlocked relationship with the actuator mechanism.

8. The scalpel handle as defined in claim 7 wherein the second biasing means biases the elongated member from its retracted condition toward its extended condition so that upon movement of the actuator mechanism into its second condition, the elongated member is automatically moved by way of the second biasing means to its extended condition for locking the actuator mechanism in its second condition.

9. The shank member as defined in claim 8 wherein the elongated member includes an accessible tab portion which accommodates the manual movement of the elongated member from its extended condition toward its retracted condition against the force of the second biasing means for releasing the actuator mechanism from its second condition.

10. A scalpel handle for holding a blade having a cutting edge, the scalpel handle comprising:

a handle member to which a blade is securable for use;

a blade shield for covering the cutting edge of the blade when the blade is secured to the handle member wherein the blade shield is connected to the handle member for pivotal movement relative thereto between a blade-covering condition at which the blade shield covers the cutting edge of the blade and an out-of-the way condition at which the cutting edge of the blade is exposed for use;

a shield latch mechanism for releasably locking the blade shield in its blade-covering condition and being connected to the handle member for movement relative thereto between one condition at which the blade shield is releasably locked in its blade-covering condition and another condition at which the blade shield is released from its locked blade-covering condition;

a manually-operable actuator mechanism which is mounted upon the handle member for movement relative thereto between a first condition and a second condition and wherein the actuator member is moved through a first phase of movement and then through a second phase of movement as the actuator mechanism is moved from the first condition to the second condition; and a linkage assembly interposed between the actuator mechanism and the blade shield; and the actuator mechanism is adapted to cooperate with the shield latch mechanism and the linkage assembly so that the manual movement of the actuator mechanism through its first phase of movement from the first condition to the second condition effects the movement of the shield latch mechanism from its one condition toward its another condition and so that the manual movement of the actuator mechanism through its second phase of movement from the first condition to the second condition effects the movement of the blade shield by way of the linkage assembly from the blade-covering condition toward the out-of-the-way condition;

a first biasing means for acting between the actuator mechanism and the handle member so that the actuator mechanism is continually biased from its second condition toward its first condition by way of the first biasing means and so that manual movement of the actuator mechanism from the first condition toward the second condition moves the actuator mechanism against the force of the biasing means; and means for releasably locking the actuator mechanism in its second condition wherein the means for releasably locking the actuator mechanism includes a movable member which is mounted upon the handle member for movement relative thereto between a locked condition at which the movable member is interlocked with the actuator mechanism when in its second condition for locking the actuator mechanism in its second condition and an unlocked condition at which the movable member is withdrawn from its interlocked relationship with the actuator mechanism; and a second biasing means for biasing the movable member from its unlocked condition toward its locked condition so that upon movement of the actuator mechanism into its second condition, the movable member is automatically moved, by way of the second biasing means, into its interlocked relationship with the actuator mechanism for locking the actuator mechanism in its second condition and thereby locking the blade shield in its out-of-the-way condition.

11. The scalpel handle as defined in claim 10 wherein the actuator mechanism and the shield latch mechanism define a first pair of cooperating cam surfaces which are engageable with one another so that movement of the actuator mechanism through its first phase of movement from the first condition to the second condition urges the actuator mechanism against the shield latch mechanism by way of the first pair of cooperating cam surfaces so that the blade latch mechanism is thereby moved from its one condition toward its another condition.

12. The scalpel handle as defined in claim 11 wherein the linkage assembly includes a lever arm which is connected to the handle member for pivotal movement relative thereto, and the actuator mechanism and the lever arm define a second pair of cooperating cam surfaces which are engageable with one another so that movement of the actuator mechanism through its second phase of movement from the first condition to the second condition urges the actuator mechanism against the lever arm by way of the second pair of cooperating cam surfaces so that the lever arm is pivoted in one direction relative to the handle member so that the blade shield is thereby moved from its blade-covering condition toward its out-of-the-way condition.

13. The scalpel handle as defined in claim 12 wherein the actuator mechanism and the lever arm define a third pair of cooperating cam surfaces which are engageable with one another so that movement of the actuator mechanism from its second condition toward its first condition urges the actuator mechanism against the lever arm by way of the third pair of cooperating cam surfaces so that the lever arm is pivoted in a direction opposite said one direction relative to the handle member so that the blade shield is thereby moved from its out-of-the-way condition toward its blade-covering condition.

14. The scalpel handle as defined in claim 10 wherein the first biasing means includes one spring for acting between the actuator mechanism and the handle member so that the actuator mechanism is continually biased from its second condition toward its first condition and so that manual movement of the actuator mechanism from the first condition and the second condition moves the actuator mechanism against the force of the one spring.

15. The scalpel handle as defined in claim 14 further comprising another spring for acting between the handle member and the shield latch mechanism for continually biasing the shield latch mechanism from its another condition toward its one condition so that the movement of the actuator mechanism through its first phase of movement from the first condition to the second condition moves the shield latch mechanism from its one condition toward its another condition against the force of the another spring.

16. The scalpel handle as defined in claim 10 wherein the handle member is elongated in shape and each of the blade shield and the actuator member is pivotally attached to the handle member for pivotal movement with respect thereto about an axis of pivot which is substantially normal to the longitudinal axis of the handle member.

17. A scalpel assembly comprising:
a blade having a cutting edge;
a handle member to which the blade is secured;
a blade shield for covering the cutting edge of the blade wherein the blade shield is connected to the handle member for pivotal movement relative thereto between a blade-covering condition at which the blade shield covers the cutting edge of the blade and an out-of-the way condition at which the cutting edge of the blade is exposed for use;
a shield latch mechanism for releasably locking the blade shield in its blade-covering condition and being connected to the handle member for movement relative thereto between one condition at which the blade shield is releasably locked in its blade-covering condition and another condition at which the blade shield is released from its locked blade-covering condition;
a spring for biasing the shield latch mechanism from its another condition toward its one condition;
a manually-operable actuator mechanism which is mounted upon the handle member for movement relative thereto between a first condition and a second condition and wherein the actuator member is moved through a first phase of movement and then through a second phase of movement as the actuator mechanism is moved from the first condition to the second condition;
a first biasing means for acting between the actuator mechanism and the handle member so that the actuator mechanism is continually biased from its second condition toward its first condition and so that manual movement of the actuator mechanism from the first condition toward the second condition moves the actuator mechanism against the force of the biasing means;
a linkage assembly interposed between the actuator mechanism and the blade shield; and
the actuator mechanism is adapted to cooperate with the shield latch mechanism and the linkage assembly so that the manual movement of the actuator mechanism through its first phase of movement from the first condition to the second condition effects the movement of the shield latch mechanism from its one condition toward its another condition and so that the manual movement of the actuator mechanism through its second phase of movement from the first condition to the second condition effects the movement of the blade shield by way of the linkage assembly from the blade-covering condition toward the out-of-the-way condition;

means for releasably locking the actuator mechanism in its second condition wherein the means for releasably locking the actuator mechanism includes a movable member which is mounted upon the handle member for movement relative thereto between a locked condition at which the movable member is interlocked with the actuator mechanism when in its second condition for locking the actuator mechanism in its second condition and an unlocked condition at which the movable member is withdrawn from its interlocked relationship with the actuator mechanism; and a second biasing means for biasing the movable member from its unlocked condition toward its locked condition so that upon movement of the actuator mechanism into its second condition, the movable member is automatically moved, by way of the second biasing means, into its interlocked relationship with the actuator mechanism for locking the actuator mechanism in its second condition and thereby locking the blade shield in its out-of-the-way condition.

18. The scalpel assembly as defined in claim 17 wherein the handle member is elongated in shape and includes two opposite side surfaces which are adapted to be grasped between the thumb and fingers of the grasping hand of an operator during use, and at least one of the side surfaces defines a plurality of circular recesses disposed thereacross for accepting the tips of the thumb or a finger of the grasping hand to facilitate the manual manipulation of the assembly while the handle member is grasped.

* * * * *